US008333686B2

(12) United States Patent
Marseille et al.

(10) Patent No.: US 8,333,686 B2
(45) **Date of Patent: *Dec. 18, 2012**

(54) CANNULA INSERTION DEVICES, SYSTEMS, AND METHODS INCLUDING A COMPRESSIBLE MEMBER

(75) Inventors: Oliver Marseille, Aachen (DE); Wolfgang Kerkhoffs, Aachen (DE)

(73) Assignee: Circulite, Inc., Saddle Brook, NJ (US)

(*) Notice: Subject to any disclaimer, the term of this patent is extended or adjusted under 35 U.S.C. 154(b) by 910 days.

This patent is subject to a terminal disclaimer.

(21) Appl. No.: 11/846,886

(22) Filed: Aug. 29, 2007

(65) Prior Publication Data

US 2008/0076960 A1 Mar. 27, 2008

Related U.S. Application Data

(63) Continuation-in-part of application No. PCT/US2007/076956, filed on Aug. 28, 2007.

(60) Provisional application No. 60/823,971, filed on Aug. 30, 2006.

(51) Int. Cl.
*A61M 1/00* (2006.01)

(52) U.S. Cl. ........................................... 600/16; 600/17

(58) Field of Classification Search ..................... 600/16
See application file for complete search history.

(56) References Cited

U.S. PATENT DOCUMENTS

| | | | |
|---|---|---|---|
| 2,935,068 | A | 5/1960 | Donaldson |
| 3,195,540 | A | 7/1965 | Waller |
| 3,433,227 | A | 3/1969 | Kettenbach |
| 3,903,895 | A | 9/1975 | Alley et al. |
| 3,942,535 | A | 3/1976 | Schulman |
| 4,033,331 | A | 7/1977 | Guss et al. |
| 4,534,761 | A | 8/1985 | Raible |
| 4,790,825 | A | 12/1988 | Bernstein et al. |
| 4,995,857 | A | 2/1991 | Arnold |
| 5,163,954 | A | 11/1992 | Curcio et al. |

(Continued)

FOREIGN PATENT DOCUMENTS

DE 102004019721 A1 10/2005

(Continued)

OTHER PUBLICATIONS

U.S. Patent and Trademark Office, International Preliminary Examination Report in PCT Application No. PCT/US07/76956, Feb. 4, 2009.

(Continued)

*Primary Examiner* — Carl H. Layno
*Assistant Examiner* — Jon-Eric C. Morales
(74) *Attorney, Agent, or Firm* — Wood, Herron & Evans, L.L.P.

(57) ABSTRACT

An insertion device for inserting a cannula through tissue generally comprises an inner shaft, a tip member coupled to a distal end portion of the inner shaft, a hollow outer shaft slidably received over the inner shaft, and a compressible member received over the inner shaft between the tip member and the outer shaft. The compressible member is configured to be received in a lumen of the cannula, and the inner shaft is movable relative to the outer shaft along an axial direction to compress the compressible member between the tip member and the outer shaft so that the compressible member expands in a generally radially outward direction. The radial expansion of the compressible member releasably secures the insertion device to the cannula.

11 Claims, 7 Drawing Sheets

14 ~12~ 224 220 218 200 180 116 112 206 126 208 208 214 102 120 122 118 216 108 104 110 224 18

U.S. PATENT DOCUMENTS 5,171,218 A 12/1992 Fonger et al.
5,190,528 A 3/1993 Fonger et al.
5,256,146 A 10/1993 Ensminger et al.
5,287,852 A 2/1994 Arkinstall
5,290,227 A 3/1994 Pasque
5,290,251 A 3/1994 Griffith
5,300,107 A 4/1994 Stokes et al.
5,338,301 A 8/1994 Diaz
5,344,443 A 9/1994 Palma et al.
5,545,191 A 8/1996 Mann et al.
5,676,670 A 10/1997 Kim
5,695,471 A 12/1997 Wampler
5,697,936 A 12/1997 Shipko et al.
5,704,891 A 1/1998 Mussivand
5,711,753 A 1/1998 Pacella et al.
5,738,649 A 4/1998 Macoviak
5,741,316 A 4/1998 Chen et al.
5,743,845 A 4/1998 Runge
5,797,960 A * 8/1998 Stevens et al. ................ 606/213
5,840,070 A 11/1998 Wampler
5,843,088 A 12/1998 Barra et al.
5,858,009 A 1/1999 Jonkman
5,921,971 A 7/1999 Agro et al.
5,924,848 A 7/1999 Izraelev
5,924,975 A 7/1999 Goldowsky
5,938,412 A 8/1999 Izraelev
5,941,813 A 8/1999 Sievers et al.
5,947,892 A 9/1999 Benkowski et al.
5,948,006 A 9/1999 Mann
5,965,089 A 10/1999 Jarvik et al.
6,001,056 A 12/1999 Jassawalla et al.
6,017,355 A 1/2000 Hessel et al.
6,116,862 A 9/2000 Rau et al.
6,176,848 B1 1/2001 Rau et al.
6,186,999 B1 2/2001 Chen
6,273,861 B1 * 8/2001 Bates et al. ................... 600/567
6,299,575 B1 10/2001 Bolling
6,354,299 B1 3/2002 Fischell et al.
6,358,266 B1 * 3/2002 Bonutti ......................... 606/190
6,406,420 B1 6/2002 McCarthy et al.
6,530,876 B1 3/2003 Spence
6,565,536 B1 5/2003 Sohn
6,605,032 B2 8/2003 Benkowski et al.
6,623,475 B1 9/2003 Siess
6,669,708 B1 12/2003 Nissenbaum et al.
6,926,662 B1 8/2005 Aboul-Hosn et al.
6,942,611 B2 9/2005 Siess
6,955,175 B2 10/2005 Stevens et al.
6,994,666 B2 2/2006 Shannon et al.
7,048,681 B2 5/2006 Tsubouchi et al.
7,070,555 B2 7/2006 Siess
7,077,801 B2 7/2006 Haverich
7,317,951 B2 1/2008 Schneider et al.
7,340,288 B1 3/2008 Karicherla et al.
7,699,864 B2 4/2010 Kick et al.
7,713,193 B2 5/2010 Nance et al.
7,722,568 B2 5/2010 Lenker et al.
7,780,692 B2 8/2010 Nance et al.
7,905,823 B2 * 3/2011 Farnan et al. ................... 600/16
2002/0010425 A1 1/2002 Guo et al.
2003/0093104 A1 5/2003 Bonner et al.
2004/0015150 A1 1/2004 Zadno-Azizi
2004/0024285 A1 2/2004 Muckter
2004/0024435 A1 2/2004 Leckrone et al.
2004/0153112 A1 8/2004 Nissenbaum et al.
2004/0193004 A1 9/2004 Tsubouchi et al.
2004/0236170 A1 11/2004 Kim
2005/0107658 A1 5/2005 Brockway
2005/0124937 A1 6/2005 Kick et al.
2005/0159711 A1 7/2005 Kathrani et al.
2006/0052750 A1 3/2006 Lenker et al.
2006/0094983 A1 * 5/2006 Burbank et al. .............. 600/567
2006/0100565 A1 * 5/2006 Aboul-Hosn ..................... 604/9
2006/0116746 A1 6/2006 Chin
2006/0135946 A1 6/2006 Moehle et al.
2006/0135962 A1 6/2006 Kick et al.
2006/0135963 A1 6/2006 Kick et al.
2006/0135981 A1 6/2006 Lenker et al.
2006/0184088 A1 8/2006 Van Bibber et al.
2006/0200189 A1 9/2006 Nance et al.
2006/0235357 A1 10/2006 Woodward et al.
2006/0253102 A1 11/2006 Nance et al.
2008/0200943 A1 8/2008 Barker et al.
2008/0215008 A1 9/2008 Nance et al.
2008/0243081 A1 10/2008 Nance et al.
2009/0112050 A1 4/2009 Farnan et al.
2009/0254166 A1 10/2009 Chou et al.
2009/0287182 A1 11/2009 Bishop et al.
2009/0287183 A1 11/2009 Bishop et al.
2010/0145267 A1 6/2010 Bishop et al.
2010/0228077 A1 9/2010 Lenker et al.

FOREIGN PATENT DOCUMENTS

EP 213748 A1 3/1987
EP 745409 A1 12/1996
WO 9742413 A1 11/1997
WO 9959652 A1 11/1999
WO 0180927 A2 11/2001
WO 2004082742 A1 9/2004
WO 2004/091716 A1 10/2004
WO 2005037345 A2 4/2005
WO 2008/034068 A2 3/2008
WO 2008027869 A2 3/2008
WO 2008034068 A2 3/2008

OTHER PUBLICATIONS

U.S. Patent and Trademark Office International Search Report and Written Opinion in PCT Application No. PCT/US2008/081082, Feb. 10, 2009.

European Patent Office, Search Report and Examiner's Preliminary Opinion, in Serial No. EP10250524, Jul. 21, 2010.

European Patent Office, Search Report and Examiner's Preliminary Opinion, in Serial No. EP10250525, Aug. 10, 2010.

U.S. Patent and Trademark Office, Notice of Allowance in U.S. Appl. No. 11/846,839, Nov. 12, 2010.

U.S. Patent and Trademark Office, Final Office Action in U.S. Appl. No. 11/846,839, Aug. 4, 2010.

U.S. Patent and Trademark Office, Non-Final Office Action in U.S. Appl. No. 12/392,623, Nov. 24, 2010.

U.S. Patent and Trademark Office, International Search Report and Written Opinion in PCT Application Serial No. PCT/US07/78507, Mar. 14, 2008.

U.S. Patent and Trademark Office, International Preliminary Report on Patentability in PCT Application No. PCT/US08/71938, Apr. 1, 2010.

U.S. Patent and Trademark Office, International Preliminary Report on Patentability in PCT Serial No. PCT/US08/081082, Apr. 26, 2010.

U.S. Patent and Trademark Office, Office Action in Serial No. 11/846,839, Apr. 29, 2010.

R J. Baird, M.D. et al., Survey of Mechanical Assistance of the Circulation and the Present Status of Left-Heart Bypass, Article, pp. 340-345, 1965.

R. J. Baird F.R.C.S.(C) et al., Le Support Mechanique Du Ventricule Gauche, Article, pp. 258-268, Dec. 1964.

World Heart Corporation, World Heart, 1998 Annual Report, 36 pgs.

U.S. Patent and Trademark Office, International Search Report and Written Opinion in PCT Application Serial No. PCT/US07/61118, Nov. 2, 2007.

U.S. Patent and Trademark Office, International Preliminary Report on Patentability PCT Application No. PCT/US08/066406, Jan. 27, 2010.

U.S. Patent and Trademark Office, International Search Report and Written Opinion in PCT Application No. PCT/US07176956, Aug. 19, 2008.

U.S. Patent and Trademark Office, Written Opinion in PCT Serial No. PCT/US08/71938, Sep. 28, 2009.

U.S. Patent and Trademark Office, International Preliminary Examination Report in PCT Serial No. PCT/US08/71922, Sep. 28, 2009.

U.S. Patent and Trademark Office, International Search Report and Written Opinion in PCT Application No. PCT/US08/66406, Oct. 8, 2008.
U.S. Patent and Trademark Office, International Search Report and Written Opinion in PCT Application No. PCT/US08/71938, Nov. 3, 2008.
U.S. Patent and Trademark Office, International Search Report and Written Opinion in PCT Application No. PCT/US08/71922, Nov. 3, 2008.
O.H. Frazier, Md et al, The HeartMate® Left Ventricular Assist System, Texas Heart Institute Journal, vol. 25, No. 4, 1998, pp. 265-271.
J. Mark Burnett, RCP et al., Intracardiac Echocardiography 101: The Beginner's Guide to ICE Imaging and Cardiac Structure Recognition, http://www.eplabdigest.com/article/4148, Dec. 13, 2007.
U.S. Patent and Trademark Office, Non-Final Office Action in U.S. Appl. No. 12/392,623, May 10, 2011.

* cited by examiner 10
12
14
16
18
20
22
24
26
28
30
34
40
42
44

CANNULA INSERTION DEVICES, SYSTEMS, AND METHODS INCLUDING A COMPRESSIBLE MEMBER

CROSS-REFERENCE

This application is a continuation-in-part of PCT Application Serial No. PCT/US07/76956 filed on Aug. 28, 2007 (pending) and claims the benefit of U.S. Provisional Patent Application Ser. No. 60/823,971, filed Aug. 30, 2006 and entitled "Devices, Methods and Systems for Establishing Supplemental Blood Flow in the Circulatory System," the disclosures of which are expressly incorporated by reference herein in their entirety. This application is also generally related to U.S. patent application Ser. No. 11/846,839 now U.S. Pat. No. 7,905,823, entitled "Devices, Methods and Systems for Establishing Supplemental Blood Flow in the Circulatory System," filed on even date herewith, which is expressly incorporated by reference herein in its entirety.

TECHNICAL FIELD

This invention generally relates to medical devices and methods and, more particularly, to devices and methods for inserting a cannula through tissue in a patient's body.

BACKGROUND

Various devices and methods have been utilized to conduct blood from the heart to assist with blood circulation in a patient. This is often desirable or necessary in cases where a patient is experiencing congestive heart failure and a transplant organ has either not been located, or the patient is not a suitable candidate for a transplant. The blood pumps are typically attached directly to the left ventricle of the heart, however, at least one blood pump system locates the pump remotely, such as subcutaneously in the manner of a pacemaker. In this regard, see U.S. Pat. No. 6,530,876, the disclosure of which is fully incorporated by reference herein. In this situation or similar situations, a cannula may be used to create an inflow conduit from the heart (an intra-thoracic location) to a pump located in a superficial (non-thoracic cavity) location, which may be the so-called "pacemaker pocket." The pacemaker pocket is a location usually accessed by a surgical incision generally parallel to and below the collarbone extending down toward the breast, and over the pectoral muscle. Sometimes the pacemaker pocket is made below the muscle. The pump, to which the cannula is connected, is intended to sit in the pacemaker pocket and is preferably at, but not limited to, a location on the right side of the chest.

General cannula implantation methods known and usable in connection with the present invention may involve many different approaches and several of the representative approaches are described further below. For example, the cannula may be implanted by directly invading the thoracic cavity. Surgical methods include so-called open heart surgery in which a median sternotomy is made to fully expose the heart within the thoracic cavity. Still other surgical methods include less invasive surgical methods such as a thoracotomy, mini-thoracotomy, thoracoscopic, or any other less invasive approaches. Any of these or other surgical methods can be used to implant the cannula in fluid communication with any desired location of the heart as described herein.

To accommodate such implantation methods and the chest anatomy of a patient, it is highly desirable for the inflow cannula to be as flexible as possible without kinking. One consideration that limits this design objective, however, is that the cannula must be of a sufficient stiffness during implantation to extend into the desired area of the patient's heart. For example, the cannula might be forced through the left atrial wall of the patient's heart to be placed in fluid communication with the left atrium. The cannula may be inserted through a hole in the atrial wall created by a dilator, the cannula itself, or another device. Therefore, devices or methods for providing the cannula with sufficient stiffness to extend through the wall of a heart without compromising the flexibility of the cannula after implantation would be desirable.

SUMMARY

An insertion device, or trocar, is provided to facilitate inserting a cannula through tissue. The insertion device generally comprises a shaft and a compressible member operatively coupled to the shaft. The shaft is configured to be received in a lumen of the cannula, and the compressible member is configured to expand in a generally radially outward direction when compressed in an axial direction. To this end, the compressible member is movable from an initial state in which it has a radial dimension smaller than the lumen of the cannula to a compressed state in which it has a radial dimension larger than the lumen of the cannula to releasably secure the insertion device to the cannula. For example, the compressible member may engage an inner wall of the cannula when expanded.

In one aspect or embodiment, the insertion device further includes a first engagement member and a second engagement member operatively coupled to the shaft. The compressible member is positioned between the first engagement member and second engagement member, which are movable relative to each other to in the axial direction to compress the compressible member therebetween.

In another aspect or embodiment, the compressible member is received on an inner shaft having a distal end portion and a proximal end portion. A tip member is coupled to the distal end portion of the inner shaft, and a hollow outer shaft is slidably received over the inner shaft in a manner such that the compressible member is positioned between the hollow outer shaft and the tip member. The inner shaft is movable relative to the hollow outer shaft along an axial direction to compress the compressible member between the tip member and the hollow outer shaft. When compressed, the compressible member expands in the generally radially outward direction to releasably secure the insertion device to the cannula.

A system for increasing blood flow between a chamber in a heart of a patient and a first location in the circulatory system of the patient is also provided. The system includes the insertion device and cannula discussed above, along with a blood pump having an inlet and an outlet. The outlet of the blood pump is adapted for connection to the first location in the circulatory system of the patient, which may be any location other than the chamber of the heart. Additionally, the cannula includes a proximal end portion configured to couple to the inlet of the blood pump and a distal end portion configured for insertion into the chamber of the heart. The insertion device is received within the lumen of the cannula so that the compressible member may be compressed in the axial direction to expand in the generally radially outward direction and thereby releasably secure the insertion device to the cannula.

Finally, a method of inserting a cannula through tissue is also provided. The method generally comprises inserting an insertion device including a distal connecting portion into a lumen of the cannula. A compressible member operatively coupled to the insertion device is then compressed in an axial direction to expand the compressible member in a generally radially outward direction. This expansion connects the distal connecting portion of the insertion device to the a distal end portion of the cannula. For example, the compressible member may engage an inner wall of the cannula when expanded. The distal end portion of the cannula is then inserted through the tissue. The method may also comprise securing the cannula to the tissue. After radially contracting the compressible member to release the distal connecting portion of the insertion device from the distal end portion of the cannula, the insertion device may be removed from the cannula.

As can be appreciated, insertion devices according to the invention will temporarily provide a cannula with the required stiffness to be directed through tissue, such as the tissue defining a wall of a patient's heart. Once the cannula is secured to the tissue of the heart and the associated insertion device is removed, the cannula may be arranged as needed to accommodate the chest anatomy of the patient. Because the insertion device is removable, the flexibility of the cannula itself need not be compromised.

Various additional features and aspects will be more readily appreciated upon review of the following detailed description of the illustrative embodiments taken in conjunction with the accompanying drawings.

DETAILED DESCRIPTION OF THE ILLUSTRATIVE EMBODIMENTS

Figure 1:
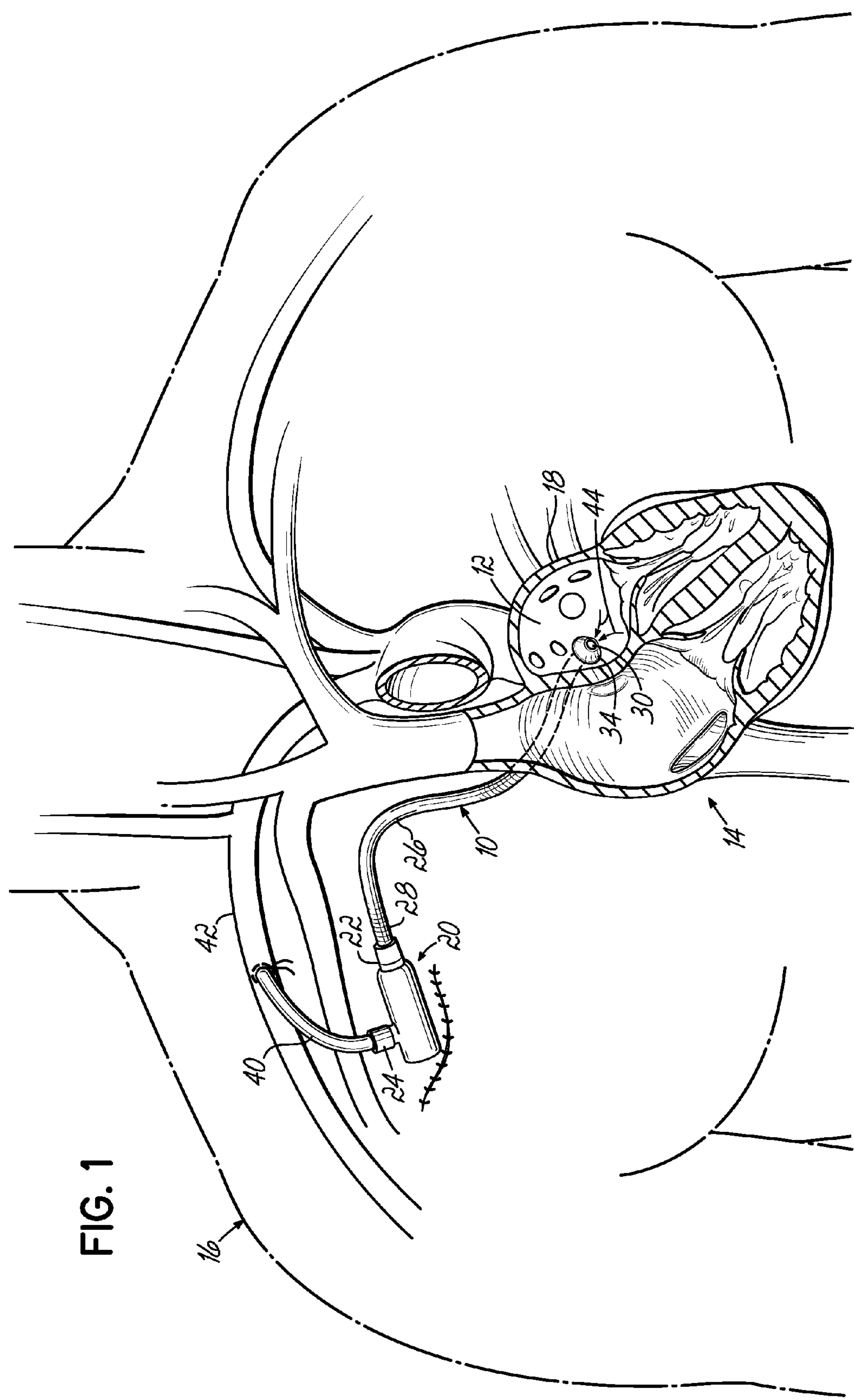
FIG. 1 is a schematic representation of chest anatomy, and illustrates one example of a blood circulation assist system implanted into a patient.

FIG. 1 illustrates one of many possible general configurations of a system 10 for increasing blood flow between a chamber 12 in a heart 14 of a patient 16 and a remote location in the circulatory system of the patient 16. The system 10 and components thereof may be implanted in any surgical manner, including by way of the surgical techniques generally discussed further below.

As shown in FIG. 1, the system 10 includes a circulatory assist device 20 having an inlet 22 and an outlet 24. The circulatory assist device 20 may be any suitable blood pump, including one of those described in U.S. Pat. Nos. 6,176,848; 6,116,862; 6,942,611; and 6,623,475 or DE 10 2004 019 721.0. An inflow cannula 26 includes a proximal end portion 28 coupled to the inlet 22 of the circulatory assist device 20 and a distal end portion 30 passing through a wall 18 of the heart 14 into the chamber 12. Although FIG. 1 shows the inflow cannula 26 extending into the left atrium, access may be made into any portion within the left side of the heart 14 (e.g., the left atrium and/or left ventricle) to access oxygenated blood.

The inflow cannula 26 may further include one or more anchor elements 34 to secure the distal end portion 30 to the wall 18. Fixation of the inflow cannula 26 may also include the application of sutures (not shown) through the wall 18 around the inflow cannula 26 in a purse-string fashion or through a portion of the anchor element(s) 34 and the wall 18. Indeed, the inflow cannula 26 may be secured to the wall 18 using any suitable technique and may be provided with any configuration or components (e.g., anchor elements) for this purpose. Alternative techniques and configurations include, without limitation, those described in the above-mentioned U.S. Provisional Patent Application Ser. No. 60/823,971.

The system 10 also includes an outflow cannula 40 connected between the outlet 24 of the circulatory assist device 20 and an artery, such as the superficial artery 42. Once the system 10 is implanted into the patient 16, oxygenated blood travels in the direction of arrows 44 from the chamber 12 (e.g., left atrium), through the inflow cannula 26, and to the circulatory assist device 20. The circulatory assist device 20, in turn, pumps the blood into the outflow cannula 40 so that the blood is supplied into the patient's arterial system.

Figure 2A:
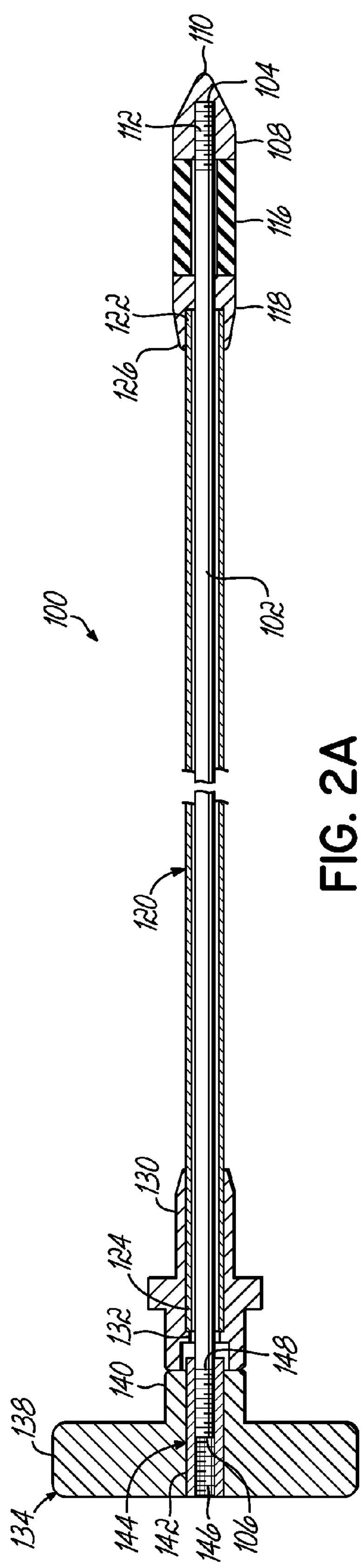
FIGS. 2A and 2B are longitudinal cross-sectional views of an insertion device according to one embodiment of the invention.
Figure 2B:
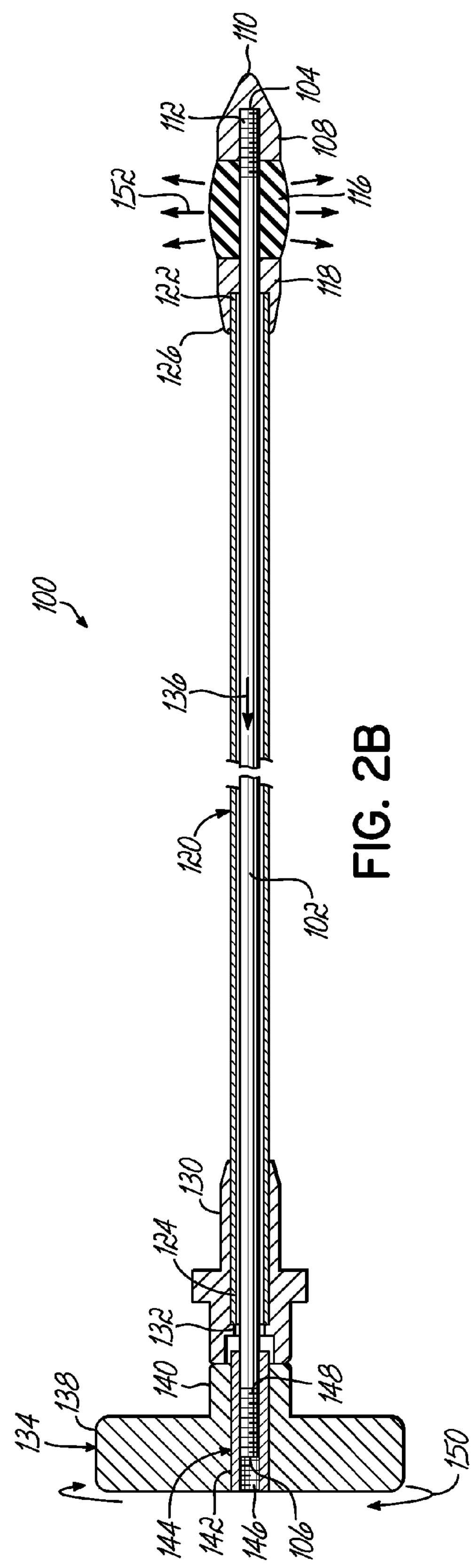

FIGS. 2A and 2B illustrate an exemplary embodiment of an insertion device 100 that may be used in the system 10 to facilitate inserting the inflow cannula 26 through the tissue. For example, the insertion device 100 may be used to facilitate inserting the inflow cannula 26 through the tissue defining the wall 18 (FIG. 1) of the heart 14 and into the left atrium or another chamber. The insertion device 100 includes an inner shaft 102, which may be solid or hollow, having a distal end portion 104 and a proximal end portion 106. A tip member 108 coupled to the distal end portion 104 tapers toward a pointed end 110 to facilitate passage of the insertion device 100 through the tissue, as will be described in greater detail below. The tip member 108 may be a separate component secured to the inner shaft 102 or may be integrally formed with the inner shaft 102. For example, the tip member 108 may be secured to the inner shaft 102 by engaging threads 112 provided around the distal end portion 104.

The insertion device 100 further includes a compressible member 116, a collar 118, and a hollow outer shaft 120 all received over the inner shaft 102. The compressible member 116, which may be constructed from an elastomeric material, is positioned between the collar 118 and the tip member 108. In one embodiment, the tip member 108, compressible member 116, and collar 118 include substantially the same or similar outer diameters. The hollow outer shaft 120 includes a distal end portion 122 and a proximal end portion 124, and is configured to slide relative to the inner shaft 102. An end portion 126 of the collar 118 may be received over the distal end portion 122 of the hollow outer shaft 120 so that the hollow outer shaft 120 engages the collar 118. To this end, the collar 118 may be press fit or otherwise secured to the hollow outer shaft 120 yet still configured to slide relative to the inner shaft 102. Alternatively, the collar 118 may be integrally formed with the hollow outer shaft 120 or simply configured to engage the hollow outer shaft 120 without being secured thereto.

A hub 130 is coupled to the proximal end portion 124 of the hollow outer shaft 120. Like the collar 118, the hub 130 may be secured onto the hollow outer shaft 120 or integrally formed therewith. The hub 130 includes a lumen 132 to allow the proximal end portion 106 of the inner shaft 102 to extend therethrough to a handle member 134 associated with the proximal end portion 106. The handle member 134 is configured to be manipulated to move the inner shaft 102 along an axial direction 136 relative to the hollow outer shaft 120, as will be described below.

Those skilled in the art will appreciate that a wide variety of handle members may be used to achieve the relative movement between the inner shaft 102 and hollow outer shaft 120. The handle member 134 shown in FIGS. 2A and 2B, however, generally includes a disk or knob 138, a cylindrical boss 140, and a bore 142 extending through the handle member 134. An actuating member 144 having internal threads 146 is received in the bore 142 and configured to engage external threads 148 provided on the proximal end portion 106 of the inner shaft 102. The actuating member 144 is press-fit within the bore 142 or otherwise secured to the handle member 134 so as to be configured to rotate therewith. Alternatively, the bore 142 may be provided with internal threads (not shown) so as to define the actuating member 144.

As shown in FIG. 2B, when the handle member 134 is rotated in a clockwise direction 150, the inner shaft 102 is moved in the axial direction 136 relative to the handle member 134. The hub 130 abuts the handle member 134 and maintains the position of the hollow outer shaft 120 such that the inner shaft 102 moves relative to the hollow outer shaft 120 as well. As the tip member 108 moves with the inner shaft 102, the compressible member 116 is compressed in the axial direction (indicated by arrow 136) between the tip member 108 and the collar 118. To this end, the tip member 108 and collar 118 serve as respective first and second engagement elements for compressing the compressible member. This compression causes the compressible member 116 to expand in a generally radially outward direction as indicated by arrows 152.

Figure 3A:
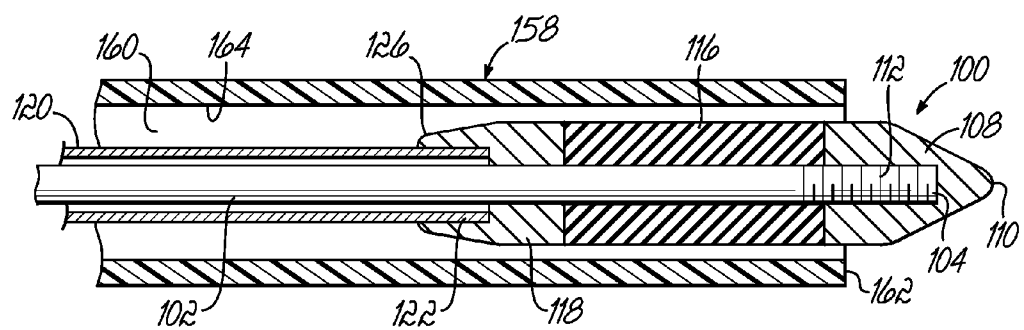
FIGS. 3A and 3B are enlarged cross-sectional views illustrating the distal end of the insertion device of FIGS. 2A and 2B being releasably secured to a cannula.
Figure 3B:
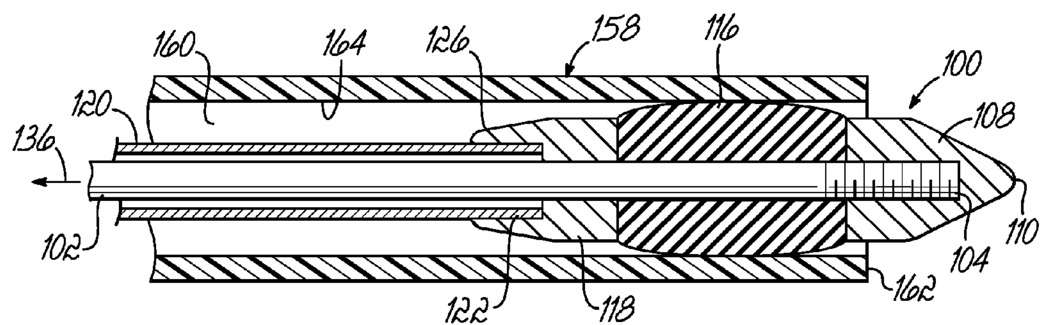

FIGS. 3A-3B illustrate how the axial expansion of the compressible member 116 may be used to releasably secure the insertion device 100 to a cannula 158. The insertion device 100 is first inserted into a lumen 160 of the cannula 158 until the tip member 108 projects beyond a distal end 162 of the cannula 158. To secure the insertion device 100, the handle member 134 (FIGS. 2A and 2B) is then rotated to move the inner shaft 102 relative to the hollow outer shaft 120 and thereby compress the compressible member 116 between the tip member 108 and collar 118. The inner shaft 102 is moved in the axial direction 136 until the compressible member 116 expands sufficiently in the generally radially outward direction 152 (FIG. 2B) to frictionally engage an inner wall 164 defining the lumen 160 of the cannula 158. This frictional engagement provides a seal so that the insertion device 100 may prevent blood loss and/or air egress into the patient's blood stream, as will be described in greater detail below.

Numerous design considerations may be optimized to provide a relatively strong frictional force between the compressible member 116 and the cannula 158. For example, the radial force applied by the compressible member 116, the amount of surface area in contact with the inner wall 164, and the geometry and material of the compressible member 116 may all contribute to this frictional engagement. Advantageously, the compressible member 116 is relatively thick so that that the frictional forces applied are greater than those associated with a balloon or other expandable member in which only a thin membrane or layer of material contacts the cannula 158. The frictional forces securing the insertion device 100 may be especially strong when the distal end 162 of the cannula 158 is rigid.

Figure 4A:
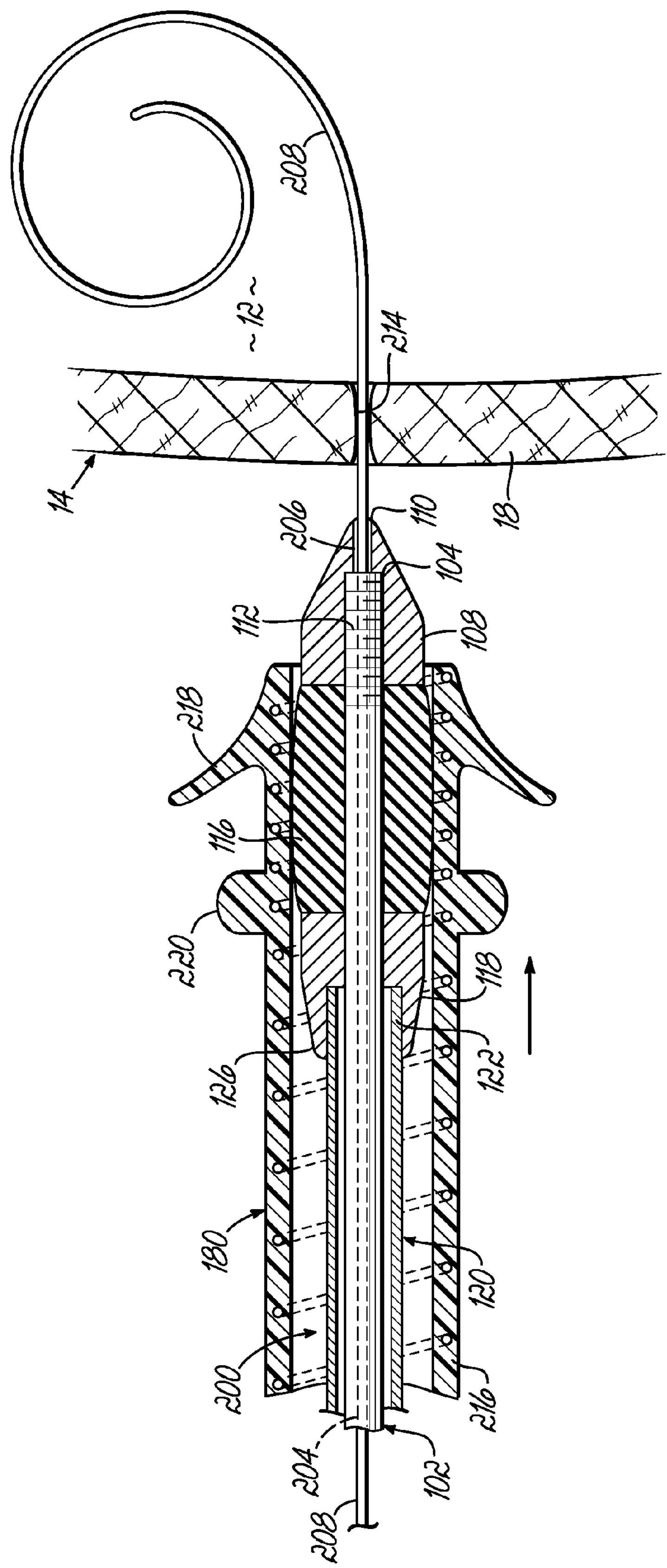
FIGS. 4A-4C are longitudinal cross-sectional views illustrating the distal end of an insertion device according to another embodiment of the invention being used to insert an inflow cannula of a blood circulation assist system through a wall of a patient's heart.
Figure 4B:
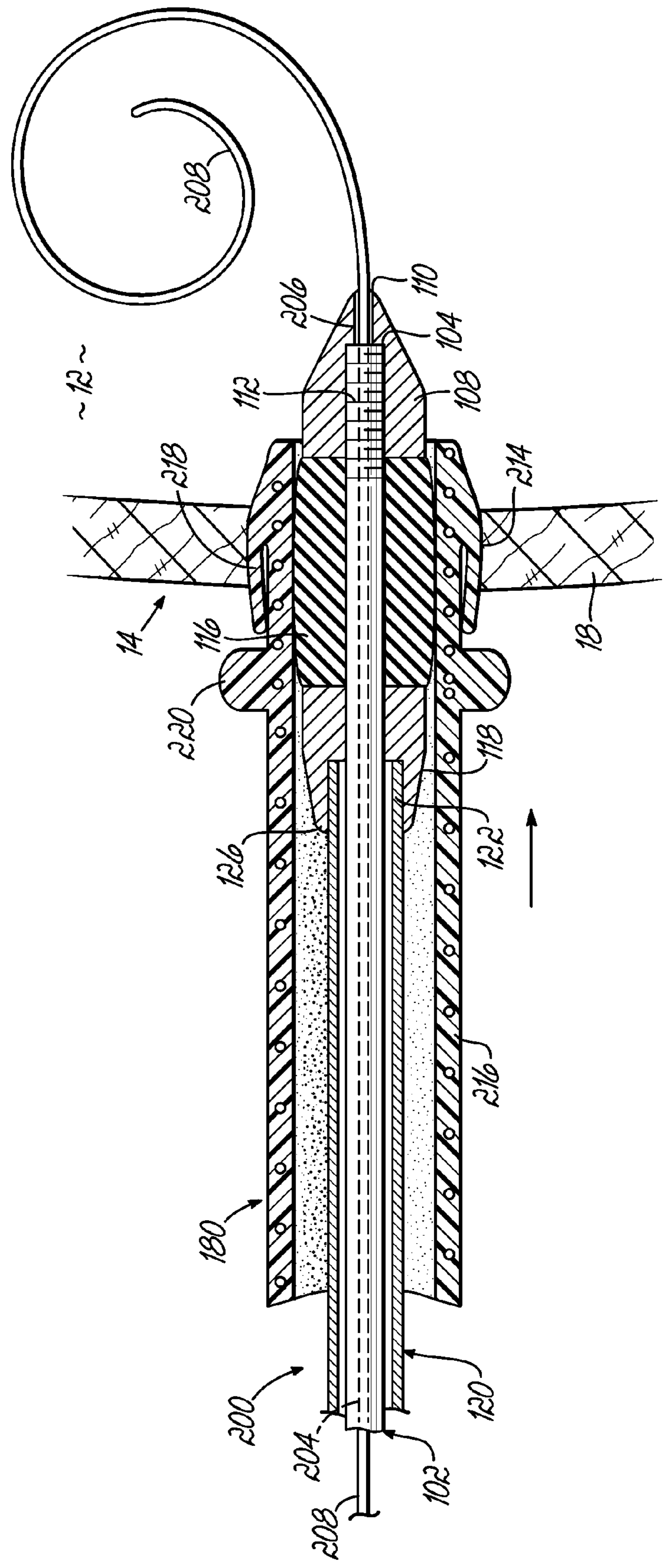
Figure 4C:
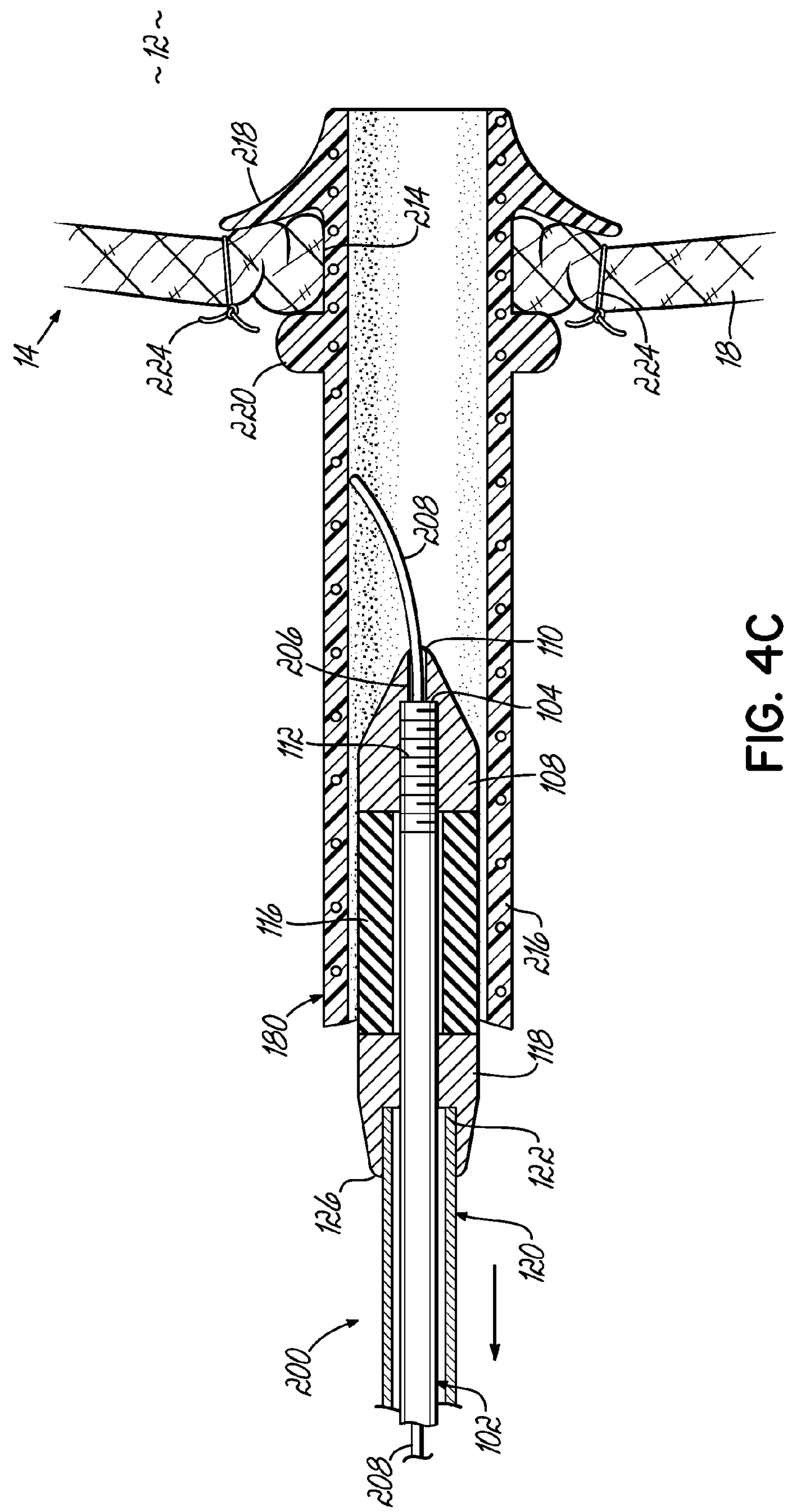

With reference to FIGS. 4A-4C, a method of inserting an inflow cannula 180 through tissue using an insertion device 200 will now be described. Although the tissue shown in FIGS. 4A-4C is the tissue defining the wall 18 of the heart 14, the method may equally apply to other tissue or organ walls not associated with the heart 14.

The insertion device 200 is substantially the same as the insertion device 100 shown in FIGS. 2A-3B. Accordingly, like reference numbers are used to refer to like structure from the embodiment shown in FIGS. 2A-3B. In this embodiment, however, the inner shaft 102 is hollow so as to include a lumen 204 extending at least partially therethrough. The tip member 108 also includes a lumen 206. Such an arrangement enables the insertion device 200 to be advanced along a guide wire 208, which extends through the lumens 204, 206.

The lumen 204 may extend completely through the inner shaft 102 so that the guide wire 208 exits the proximal end portion 106 as the insertion device 200 is advanced. It will be appreciated, however, that the guide wire 208 may alternatively exit a side opening (not shown) provided on the inner shaft 102. Additionally, the insertion device 200 may be configured such that the guide wire 208 only passes through the tip member 108. The insertion device 200 may be secured to the inflow cannula 180 prior to or after receiving the guide wire 208 in the same manner described above with reference to the cannula 158.

The inflow cannula 180 generally includes a main body 216, a flared tip portion 218, and a ring member 220 spaced from the flared tip portion 218. As with the inflow cannula 26 (FIG. 1), the inflow cannula 180 is merely one example of a cannula that may be used in the system 10. The flared tip portion 218 and ring member 220 serve a similar function as the anchor element 34 (FIG. 1). Thus, although the flared tip portion 218 and ring member 220 are described briefly below, those skilled in the art will appreciate that the inflow cannula 180 may have other configurations and/or include other components.

As the insertion device 200 and inflow cannula 180 are advanced along the guide wire 208, they are directed to the wall 18 of the heart 14. The tip member 108 first contacts the wall 18 and acts as a dilator because of its pointed end 110. In other words, the tip member 108 gradually expands an opening 214 in the wall 18 so that the opening 214 can accommodate the inflow cannula 180 more easily.

As shown in FIG. 4B, when the inflow cannula 180 is passed through the wall 18, the flared tip portion 218 flexes inwardly toward the main body 216. The inflow cannula 180 is further advanced until both the flared tip portion 218 and ring member 220 are positioned in the chamber 12, which may be the cavity of the left atrium. The flared tip portion 218 flares back to its original shape once it passes through the wall 18, and the inflow cannula 180 is then retracted to pull the ring member 220 back through the opening 214. Advantageously, the flared tip portion 218 captures loose tissue produced as a result of the inflow cannula 180 being inserted through the opening 214 and seals against the wall 18 upon retraction of the ring member 220.

As shown in FIG. 4C, purse string sutures 224 may then be used to help secure the wall 18 around the inflow cannula 180 between the flared tip portion 218 and the ring member 220. Again, such an arrangement is merely one example of how the inflow cannula may be secured to the atrial wall. The method described herein for inserting the inflow cannula may be used with a wide variety of other cannulas and techniques for securing such cannulas to the wall of a heart. Accordingly, those skilled in the art will appreciate that the method is not limited to the specific inflow cannula and attachment technique described above. For example, additional techniques for securing a cannula to a wall of a heart are shown and described in U.S. Provisional Patent Application Ser. No. 60/823,971.

Once the inflow cannula 180 is secured to the tissue of the wall 18 surrounding the opening 214, the handle member 134 (FIGS. 2A and 2B) may be rotated in an opposite direction to move the inner shaft 102 back toward its initial position relative to the hollow outer shaft 120. As the tip member 108 moves along with the inner shaft 102, the compressible member 116 is able to lengthen in an axial direction to reduce or contract the radial dimension thereof. Eventually the compressible member 116 radially contracts back into its initial state and releases the insertion device 200 from the inflow cannula 180. When this occurs, the insertion device 200 and guide wire 208 may then be removed from the inflow cannula 180.

Thus, the insertion device 200 temporarily provides at least the distal portion of the inflow cannula 180 with sufficient rigidity during insertion through the wall 18 of the heart 14. This enables the inflow cannula 180 to be designed with optimal flexibility. In other words, the flexibility of the inflow cannula 180 does not need to be compromised to ensure that the inflow cannula 180 is able to extend through the opening 214 in the wall 18. Because the insertion device 200 may be removed after the inflow cannula 180 is secured to the wall 18, the inflow cannula 180 can still be manipulated as desired around the patient's chest anatomy.

When the guide wire 208 is not required to establish an initial path leading to the wall 18 of the heart 14, the insertion device 100 (FIGS. 3A and 3B) may be used instead of the insertion device 200 to insert the inflow cannula 180 through the wall 18. The insertion device 100 is substantially similar to the insertion device 200, but does not include the lumen 204 and the lumen 206 for accommodating the guide wire 208. As a result, when the compressible member 116 is compressed in the axial direction 136 so that it expands in a radial direction to secure the insertion device 100 to the inflow cannula 180, the compressible member 116 may provide a seal between the insertion device 100 and inflow cannula 180. The seal advantageously protects against blood loss and/or air ingress into the blood.

For example, after the tip member 108 is pushed against the wall 18 to form and expand the opening 214, pressures within the heart 14 may cause blood to attempt to exit the heart 14 through the inflow cannula 180. Patients with high blood pressures may be particularly susceptible to such blood loss through the inflow cannula 180. However, by providing a seal between the insertion device 100 and the inflow cannula 180, the compressible member 116 prevents this blood loss while the inflow cannula 180 is secured to the tissue of the wall 18 surrounding the opening 214 (by forming the purse string sutures 224, etc.).

Once the inflow cannula 180 is secured to the wall 18, the handle member 134 may be manipulated to lengthen the compressible member 116 an initial distance in an axial direction. The initial distance may be long enough to reduce the radial force applied by the compressible member 116 against the inflow cannula 180, yet small enough to maintain the seal with the inflow cannula 180. For example, the radial force applied by the compressible member 116 may be reduced until a surgeon is able to slide the insertion device 100 relative to the inflow cannula 180. The insertion device 100 may be pulled back through the inflow cannula 180, which remains secured to the wall 18 of the heart 14. Because the compressible member 116 can still provide a seal between the insertion device 100 and inflow cannula 180 during this relative movement, the insertion device 100 may function like a piston that removes air. In particular, the insertion device 100 may create a vacuum as it is retracted to draw blood from the heart 14 into the inflow cannula 180. The blood replaces air that previously occupied the inflow cannula 180.

Once the insertion device 100 has been pulled through a first portion of the inflow cannula 180 to fill the first portion with blood, the first portion may be clamped or otherwise sealed off from a second portion of the inflow cannula 180 still occupied by the insertion device 100. Next, the insertion device 100 may be completely removed from the inflow cannula 180. If desired, the handle member 134 may first be manipulated to lengthen the compressible member 116 an additional distance in the axial direction to further reduce the radial force applied against the inflow cannula 180. Because the first portion of the inflow cannula 180 has been clamped or sealed off, the compressible member 116 may even be lengthened until it no longer maintains a seal between the insertion device 100 and the inflow cannula 180. This allows the insertion device 100 to be more easily pulled through and removed from the inflow cannula 180.

After removing the insertion device 100, the inflow cannula 180 may be connected to the other components in the system 10 (FIG. 1). For example, the inflow cannula may then be connected to the inlet 22 of the circulatory assist device 20. The clamp or other structure sealing off the first portion of the inflow cannula 180 may be released once this connection is sealed against blood loss.

Figure 5A:
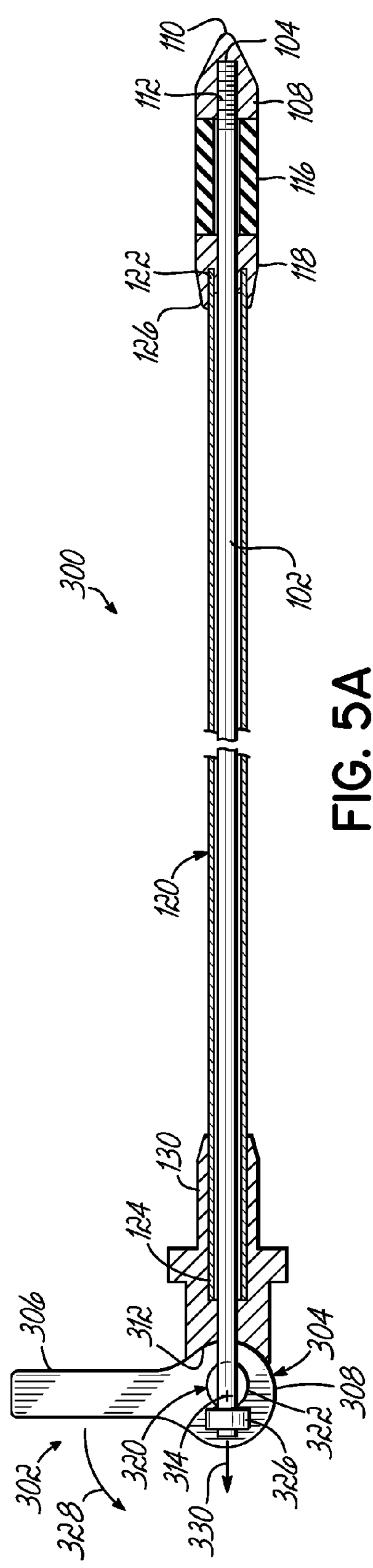
FIGS. 5A-5C are longitudinal cross-sectional views of an insertion device according to yet another embodiment of the invention.
Figure 5B:
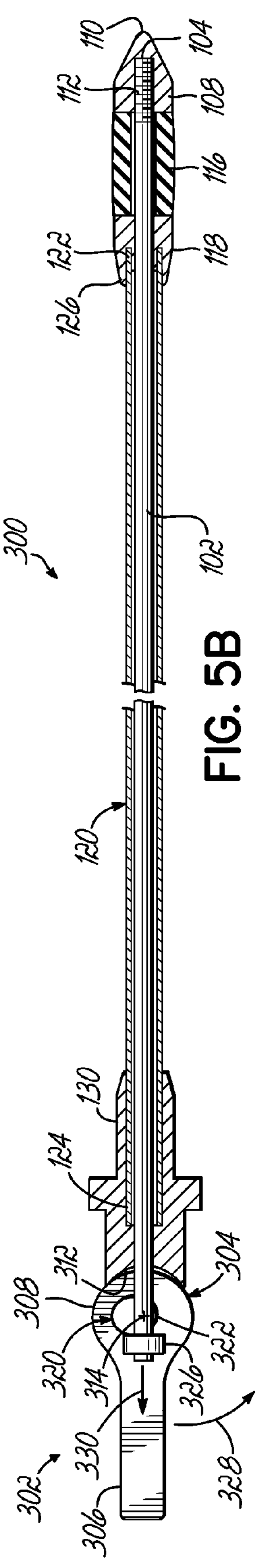
Figure 5C:
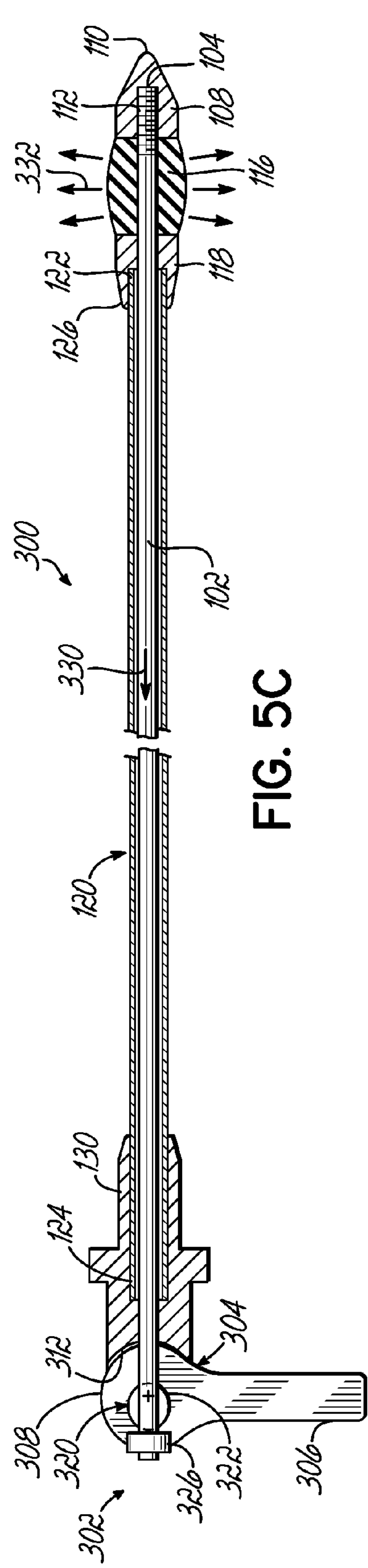

FIGS. 5A-5C illustrate an insertion device 300 according to an alternative embodiment. Again, the insertion device 300 is substantially similar to the insertion devices 100, 200 such that like numbers are used to refer to like structure from the insertion devices 100, 200. In this embodiment, the insertion device 300 includes a handle member 302 having a joint portion 304 and a toggle or lever portion 306 extending from the joint portion 304. The joint portion 304 includes an outer surface 308 having a round or substantially circular cross-sectional profile, and the hub 130 includes a rear surface 312 generally shaped to conform to the outer surface 308 of the joint portion 304. Such an arrangement enables the handle member 302 to rotate relative to the hub 130 and hollow outer shaft 120 about an axis 314.

The handle member 302 further includes an eccentric bolt 320 extending at least partially therethrough. In other words, the center of the bolt 320 is offset from the axis 314. The bolt 320 has an elliptical cross-sectional configuration and, despite its offset arrangement, includes a portion 322 that overlaps the axis 314.

A tab or protrusion 326 coupled to the proximal end portion 106 of the inner shaft 102 is configured to contact the bolt 320 as the handle member 302 rotates. For example, FIG. 5A shows the insertion device 300 in a initial position with the toggle 306 of the handle member 302 angled approximately 90° relative to the inner shaft 102, the compressible member 116 in a uncompressed state, and the tab 326 contacting the bolt 320 and positioned a first distance away from the axis 314. To compress the compressible member 116 between the tip member 108 and collar 118, the handle member 302 is rotated in the direction 328. As the handle member 302 rotates, the bolt 320 moves the tab 326 further away from the axis 314 in an axial direction 330 due to the eccentric arrangement of the bolt 320. Thus, by the time the toggle 306 is rotated approximately 180° (FIG. 5C), the tab 326 is positioned a second distance away from the axis 314 (with the second distance greater than the first distance).

The inner shaft 102 moves in the axial direction 330 along with the tab 326 while the handle member 302 maintains the hub 130 and hollow outer shaft 120 in substantially the same position. As a result, the inner shaft 102 moves relative to the hollow outer shaft 120 to compress the compressible member

116 between the tip member 108 and the collar 118. The compressible member 116 expands in a generally radially outward direction as indicated by arrows 332 when compressed in the axial direction as indicated by arrow 330 in the same manner as described above with reference to the insertion devices 100 and 200. Thus, reference can be made to FIGS. 3A-4C and the description thereof for an understanding of how the insertion device 300 may be releasably secured to a cannula to facilitate inserting the cannula through the wall of a heart.

To release the cannula, the handle member 302 may simply be rotated back to its initial position. This allows the compressible member 116 to radially contract to its uncompressed shape, which causes the tip member 108 to move away from the hollow outer shaft 120 and collar 118. As a result, the inner shaft 102 moves relative to the hollow outer shaft 120, hub 130, and handle member 302 such that the tab 326 remains in contact with the bolt 320. Although not shown in FIGS. 5A-5C, it will be appreciated that the described operation of the insertion device 300 will allow temporary attachment of the insertion device 300 to the distal end of a cannula for stiffening the same during movement through tissue.

Other aspects relating to the surgical implantation of the inflow cannula 180 are not described in detail because the insertion device 100, 200 or 300 may be used to facilitate implantation of the inflow cannula 180 and other cannulas in a wide variety of surgical approaches. Non-limiting examples of such surgical approaches are briefly described below.

Surgical Open Sternotomy—This approach allows full access to the heart, especially the left atrium, and allows access to several different locations where a blood inflow cannula might be attached to the heart. However, due to the highly invasive nature of this approach, less invasive implantation approaches may be more desirable to a surgeon.

Surgical Open Thoracotomy—In this surgical approach, a relatively superior and caudal thoracotomy access is used to deliver the inflow cannula to the left atrium where it is anchored. This location on the atrium has specific benefit because the wall of the atrium is smooth and relatively large at this location, isolating the cannula tip from other structures within the atrium.

In another suitable surgical method, a relatively lateral thoracotomy access is used to deliver the blood inflow cannula to the left atrium where it is anchored at a location on the postero-medial wall near the interatrial septum. This location is often called “Waterson’s groove” and is a common location to make a left atriotomy when performing mitral valve repair surgery. Waterson’s groove terminates between the superior vena cava and the left pulmonary veins at the left atrium.

Thoracoscopic Surgery—In this surgical method, a blood inflow cannula may be implanted in a similar location as described above in that a tubular trocar may be used to access the intra-thoracic location (Waterson’s groove, for example) where the cannula would be anchored through the heart wall. In this minimally or less invasive surgical method, the entire operation is performed through these relatively small tubular trocars thereby minimizing the size of the opening in the patient’s chest. Typically, additional small holes are made to deliver trocars used in conjunction with the main delivery trocar to allow placement of an endoscopic camera and specialized surgical tools for grasping, cutting, suturing, cauterizing, or performing other operations on tissue. Through the main trocar, the inflow cannula can be delivered to the same location as in the open surgical technique (i.e. Waterson’s groove) but with less invasive access across the chest wall.

Over-the-Wire (Seldinger) Technique—A variation of the Seldinger technique might be utilized in the various surgical implantation approaches described above, where the cannula system would be specifically adapted to facilitate this implantation technique. Although the Seldinger technique is most commonly associated with percutaneous access to blood vessels, an adapted version of the technique utilizing a specifically adapted cannula introduction system is a highly preferred approach to surgical implantation where direct access to the heart itself is utilized. Here, for example, an atriotomy could be made by inserting a needle across the heart wall and a guidewire then placed therethrough. After removal of the needle, with bleeding controlled and minimal, the cannula system with specialized insertion device within can be introduced over the wire thereby maintaining many of the advantages of the so-called Seldinger technique even in a surgical approach.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. For example, the insertion devices disclose herein may alternatively be used to insert a cannula through a wall of a kidney or other organ or body cavity (not shown). Additionally, the bolt 320 in FIGS. 5A-5C may have a circular or any other desired cross-sectional profile instead of an elliptical profile. The invention in its broader aspects is therefore not limited to the specific details, representative apparatus and methods and illustrative examples shown and described. The various features of the invention may be used alone or in any combination depending on the needs and preferences of the user. Accordingly, departures may be made from such details without departing from the scope or spirit of the general inventive concept.

What is claimed is:

1. A cannula assembly, comprising:

a cannula having an inner wall defining a lumen; and an insertion device including:

(a) a shaft including a distal end, the shaft configured to be received within the lumen of the cannula;

(b) a tip member coupled to the distal end of the shaft, the tip member configured to extend distally out from the lumen of the cannula so as to be in position for dilating a puncture in a tissue;

(c) a compressible member operatively coupled to the shaft and configured to expand in a generally radially outward direction when compressed in an axial direction;

wherein the compressible member is movable from an initial state in which the compressible member has a first radial dimension to a compressed state in which the compressible member has a second radial dimension that is larger than the first radial dimension, the second radial dimension configured to engage the inner wall of the lumen of the cannula to releasably secure the insertion device to the cannula.

2. A method of inserting a cannula through tissue, the cannula including a lumen and a distal end portion, the method comprising:

inserting an insertion device including a distal connecting portion into the lumen of the cannula wherein the distal connecting portion comprises an inner shaft having a distal end, a tip member coupled to the distal end of the inner shaft, and a compressible member operably coupled to the inner shaft;

compressing the compressible member of the insertion device in an axial direction to expand the compressible member in a generally radially outward direction so as to connect the distal connecting portion of the insertion device to the distal end portion of the cannula; and inserting the distal end portion of the cannula through the tissue while the distal connecting portion is connected to the distal end portion by exerting a pushing force on the insertion device.

3. The method of claim 2 wherein the tissue defines a wall of a chamber of a heart, and wherein inserting the distal end portion of the cannula through the tissue comprises inserting the distal end portion of the cannula into the chamber of the heart.

4. The method of claim 2, further comprising:

securing the cannula to the tissue;

radially contracting the compressible member to release the distal connecting portion of the insertion device from the distal end portion of the cannula; and removing the insertion device from the cannula.

5. The method of claim 2, the insertion device further comprising a hollow outer shaft slidably positioned over the inner shaft, the compressible member being received on the inner shaft between the hollow outer shaft and the tip member, and wherein compressing the compressible member further comprises:

moving the inner shaft relative to the hollow outer shaft along the axial direction so that the compressible member is compressed between the hollow outer shaft and the tip member.

6. The method of claim 5 wherein moving the inner shaft relative to the hollow outer shaft further comprises:

manipulating a handle member associated with the inner shaft.

7. The method of claim 2 wherein compressing the compressible member causes the compressible member to exert a radial force against an inner wall of the cannula and to form a seal between the distal connecting portion of the insertion device and the distal end portion of the cannula, the method further comprising:

radially contracting the compressible member an initial amount to reduce the radial force applied by the compressible member against the cannula, wherein the compressible member maintains the seal between the insertion device and the cannula when radially contracted the initial amount; and retracting the distal connecting portion of the insertion device at least partially through the lumen of the cannula.

8. The method of claim 7 wherein the distal connecting portion engages the cannula at a first portion of the lumen and retracting the insertion device moves the distal connecting portion from the first portion of the lumen to a second portion of the lumen so as to draw blood into the first portion of the lumen, the method further comprising:

forming a seal between the first portion of the cannula and a second portion of the cannula, the second portion being at least partially occupied by the distal connecting portion of the insertion device after retracting the distal connecting portion; and removing the insertion device from the cannula after forming the seal.

9. The method of claim 8, further comprising:

radially contracting the compressible member an additional amount before removing the insertion device from the cannula to release the distal connecting portion from the second portion of the cannula.

10. The method of claim 9, further comprising:

coupling the cannula to an inlet of a blood pump; and releasing the seal formed between the first portion and second portion of the cannula.

11. A system for increasing blood flow between a chamber in a heart of a patient and a first location in the circulatory system of the patient remote from the chamber, the system comprising:

a blood pump having an inlet and an outlet, the outlet being adapted for connection to the first location in the circulatory system of the patient;

a cannula having an inner wall defining a lumen, a proximal end portion configured to couple to the inlet of the blood pump, and a distal end portion configured for insertion into the chamber of the heart; and an insertion device for assisting with insertion of the distal end of the cannula into the chamber of the heart, including a shaft including a distal end, the shaft configured to be received within the lumen of the cannula;

a tip member coupled to the distal end of the shaft, the tip member configured to extend distally out from the lumen of the cannula so as to be in position for dilating a puncture in the tissue; and a compressible member operatively coupled to the shaft and configured to expand in a generally radially outward direction when compressed in an axial direction;

wherein the compressible member is movable from an initial state in which the compressible member has a first radial dimension to a compressed state in which the compressible member has a second radial dimension that is larger than the first radial dimension, the second radial dimension configured to engage the inner wall of the lumen of the cannula to releasably secure the insertion device to the cannula.

* * * * *